United States Patent
Bailey et al.

(10) Patent No.: US 7,735,350 B2
(45) Date of Patent: Jun. 15, 2010

(54) MEASURING INTENSITY OF SHOT PEENING IN AREAS WITH DIFFICULT ACCESSIBILITY

(75) Inventors: Peter Gregory Bailey, Hamilton, OH (US); Gerard Gilmary Burns, Mason, OH (US)

(73) Assignee: General Electric Co., Schenectady, NY (US)

( * ) Notice: Subject to any disclaimer, the term of this patent is extended or adjusted under 35 U.S.C. 154(b) by 44 days.

(21) Appl. No.: 12/240,185

(22) Filed: Sep. 29, 2008

(65) Prior Publication Data

US 2010/0077831 A1    Apr. 1, 2010

(51) Int. Cl.
    *G01L 5/00* (2006.01)
(52) U.S. Cl. .................. 73/11.02; 73/12.09
(58) Field of Classification Search .......... 73/11.02, 73/12.09
    See application file for complete search history.

(56) References Cited

U.S. PATENT DOCUMENTS

| | | | |
|---|---|---|---|
| 2,350,440 A * | 6/1944 | Almen .............. 73/11.02 |
| 2,958,925 A | 11/1959 | Roberts |
| 3,695,091 A | 10/1972 | Smith |
| 4,102,176 A | 7/1978 | Fuchs |
| 4,120,930 A * | 10/1978 | Lemelson .............. 264/225 |
| 4,402,227 A | 9/1983 | Hayashi et al. |
| 4,470,292 A * | 9/1984 | DeClark et al. .......... 73/11.02 |
| 4,709,383 A | 11/1987 | Goto et al. |
| 4,864,867 A | 9/1989 | Manahan, Sr. |
| 5,204,826 A | 4/1993 | Thompson et al. |
| 5,297,418 A | 3/1994 | Champaigne |
| 5,350,161 A | 9/1994 | Perrotti |
| 5,581,483 A | 12/1996 | Thompson et al. |
| 5,625,664 A | 4/1997 | Berkley |
| 5,674,328 A * | 10/1997 | Mannava et al. ............ 148/525 |
| 5,674,329 A * | 10/1997 | Mannava et al. ............ 148/525 |
| 5,731,509 A | 3/1998 | Thompson |
| 5,780,714 A * | 7/1998 | Champaigne ............. 73/1.79 |
| 5,877,405 A | 3/1999 | Champaigne |
| 5,948,293 A | 9/1999 | Somers et al. |

(Continued)

OTHER PUBLICATIONS

Bill Barker, Shotmeter A New Tool for Evaluating Shot Peening Intensity, 2000.*
Ciampini, Characterization of vibratory finshing using the Almen system, Jul. 19, 2007.*

(Continued)

*Primary Examiner*—Lisa M Caputo
*Assistant Examiner*—Freddie Kirkland, III
(74) *Attorney, Agent, or Firm*—William Scott Andes; Steven J. Rosen

(57) ABSTRACT

Determining shot peening intensity by affixing a Almen test strip to a shot peening surface, removing the peened strip from the shot peening surface, measuring an arc height of the shot peened strip, and determining peening intensity on the surface from the measured arc height. The strip may be affixed with an adhesive such as rubber cement and may be a sub-size strip cut from a full size Almen strip. The arc heights of the sub-size strip may be correlated to arc heights of the standard strips. A sub-size strip may be affixed to and a full size standard strip may be mounted on a peening surface of a block and be simultaneously shot peened. Arc heights may be measured on a gage having support means for holding both strips.

23 Claims, 7 Drawing Sheets

U.S. PATENT DOCUMENTS

| | | |
|---|---|---|
| 6,183,882 B1 | 2/2001 | Mannava et al. |
| 6,289,713 B1 | 9/2001 | Champaigne |
| 6,415,044 B1 | 7/2002 | Simpson et al. |
| 6,568,239 B1 | 5/2003 | Champaigne |
| 7,185,521 B2 | 3/2007 | Lombardo et al. |
| 7,210,322 B2 | 5/2007 | Iwata |

OTHER PUBLICATIONS

EI Electronics Incorporated, shot peening control technology, Almen Products, http://www.shotpeener.com Sep. 22, 2008, 2 pages.

"Metallic Shot Peening For Critical Applications", GE Aircraft Engines, Specification No. P11TF8, Issue No. S10, Sep. 13, 2004, 2 pages.

* cited by examiner

MEASURING INTENSITY OF SHOT PEENING IN AREAS WITH DIFFICULT ACCESSIBILITY

BACKGROUND OF THE INVENTION

1. Field of the Invention

This invention relates to shot peening and, more particularly, to measuring shot peening intensity with Almen test strips.

2. Description of Related Art

Shot peening has been common practice in the treatment of metal components to increase or restore fatigue life. Spherical shot is impacted on the surface of a component forming very small spherical dents on the surface and imparting compressive residual stress in the component in the shot peened surface of the component. It is highly desirable if not required to control intensity of the shot peening because intensity above and below a critical intensity range can result in a component having less than optimal fatigue life properties.

Shot is typically accelerated by using air pressure to force the shot through a peening nozzle which is directed at the surface undergoing peening. Almen strips are used to measure shot peening intensity by their curvature which is typically referred to as arc height. Note that arc height or curvature is sometimes referred to as deflection. Almen strips are precision (hardness and thickness controlled) thin 1070 steel strips. Each strip is bolted to a holder which restrains the strip from curving until the bolts are released. The strip is then exposed to the shot stream under the same conditions as the component undergoing peening. After the strip has undergone peening for a predetermined time period, the strip is removed from the holder and the arc height (curvature) measured, all according to specification prescribed procedures, using an Almen gage containing a dial (or digital) indicator or gage. Typically, a scrap part is appended with a number of Almen strip holders so that intensity may be determined in a number of locations.

Accordingly, a series of Almen strips are exposed to the shot stream for increasing time periods at each of these locations. When the arc height of each of the Almen strips increases by no more than ten percent (10%) when the time is doubled, the arc height is declared to be the intensity and peening of the component parts may begin at this intensity if all are within the required range. Intensity is expressed in terms of measurement of the arc height, e.g. inches.

Intensities in less accessible areas, where holders cannot fit, can sometimes be inferred by similarity in impingement angle to Almen strip equipped areas. In critical life areas inference is often not enough. In areas that are smaller than the Almen strip or accessible only by ricochet, a better method is highly desirable. One method uses "shaded" strips in which a full strip is mounted in a fixture exposing only a stripe representing the size, location and accessibility issues of the part area to be shot peened. The use of "shaded" strips in small areas involves an expensive tooling cost to insert the shaded strip holder into a fixture simulating the part to be peened. The use of "shaded" strips requires an added step in the peening process setup because an additional setup and peening test must be conducted to correlate the shaded strip arc height to full strip values which must be within the required intensity range. A more accurate, less costly, and less time consuming shot peening intensity measuring method is highly desirable.

SUMMARY OF THE INVENTION

A method of determining shot peening intensity on a shot peening surface of a workpiece includes (a) affixing an Almen test strip to a shot peening surface; (b) removing the peened Almen test strip from the shot peening surface; (c) measuring the arc height of the shot peened Almen test strip; and (d) determining the shot peening intensity on the shot peening surface from the measured arc height. An exemplary embodiment of the method includes using an adhesive for affixing the Almen test strip to the shot peening surface such as rubber cement. A sub-size embodiment of the test strip may be used. The sub-size embodiment of the test strip is made by cutting it from a full size standard Almen strip. An A, N, or C type Almen strip may be used for the full size standard Almen strip.

The method may further include correlating arc heights of the sub-size test strip to arc heights of the standard Almen strips. The correlating may also include affixing a sub-size Almen test strip to a two strip shot peening surface of a shot peening block (also referred to as an Almen block), mounting a full size standard Almen strip to the block, and simultaneously shot peening the sub-size Almen test strip and the full size standard Almen strip mounted on the block. This correlation may be done at process set up. This may be performed by mounting one or more the two strip shot peening blocks around a scrap or other part or workpiece and simultaneously shot peening the sub-size Almen test strips and the full size standard Almen strips mounted on the blocks.

The arc height of the shot peened sub-size Almen test strip and the full size standard Almen strip may be measured on an Almen gage having end and rear locating first pins for positioning the full size standard Almen strip and 4 magnetic support balls for holding the full size standard Almen strip during measuring of the arc height. One or more additional sets of magnets are used to hold the sub-size Almen test strip or strips during measuring of the arc height. The end and rear locating first pins, the magnetic support balls, and the one or more additional sets of magnets are mounted on a base of the Almen gage, and they are sized and located for measuring the arc height of the full size standard Almen strip and the sub-size Almen test strip with a single dial or digital indicator or other arc height measuring device. The one or more additional sets of magnets are set closer together than and are located inside of the magnetic support balls. The magnetic support balls and the one or more additional sets of magnets are centered around a hole in the base and the dial or digital indicator or the other arc height measuring device has a spindle extending through the hole in the base. A second set of locating pins for positioning the sub-size Almen test strip may also be mounted on the base.

BRIEF DESCRIPTION OF THE DRAWINGS

The foregoing aspects and other features of the invention are explained in the following description, taken in connection with the accompanying drawings where.

DETAILED DESCRIPTION OF THE INVENTION

Figure 1:
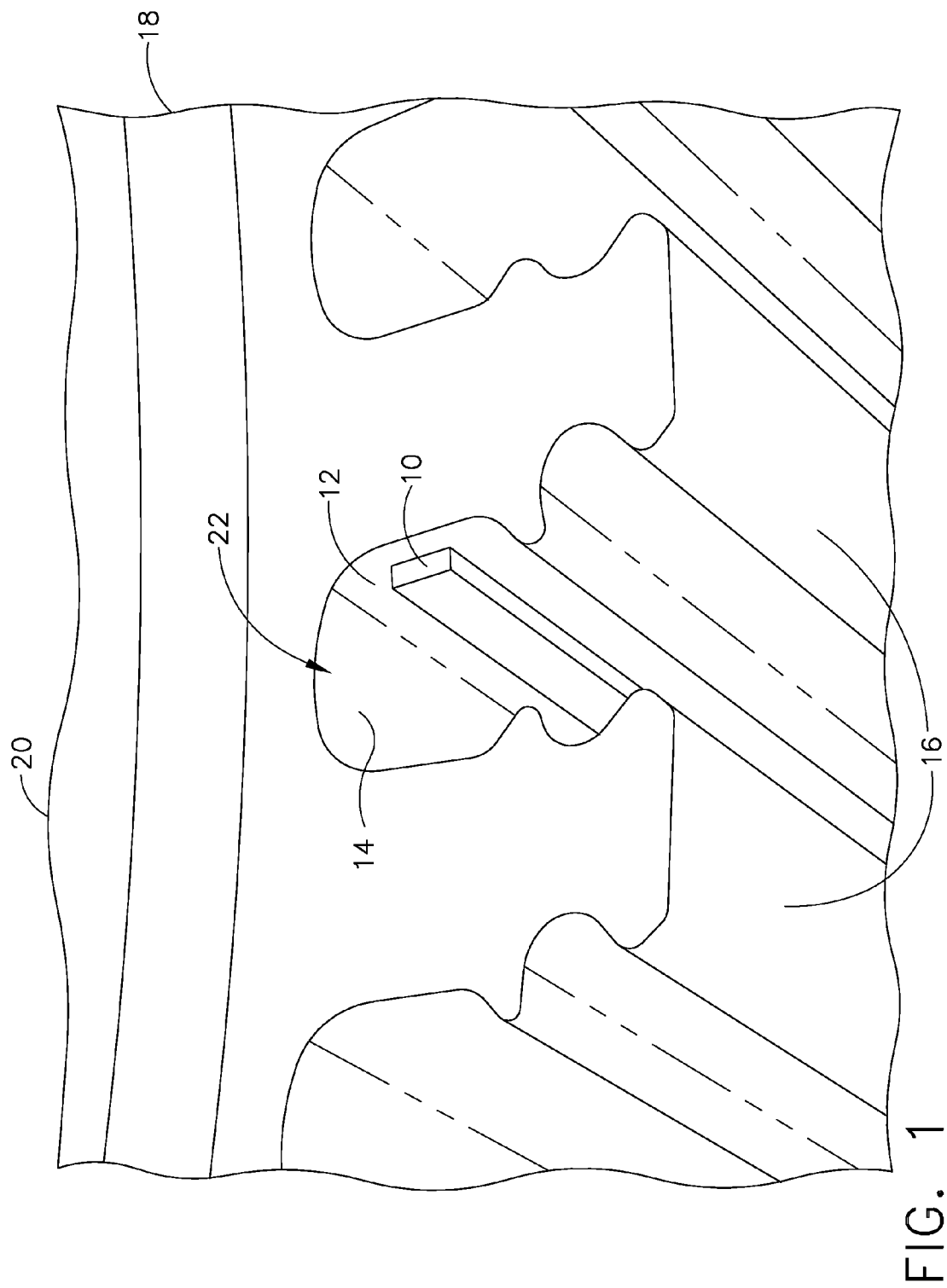
FIG. 1 is a perspective view illustration of a sub-size Almen test strip affixed to a shot peening surface in a dovetail blade slot in a gas turbine engine disk.
Figure 2:
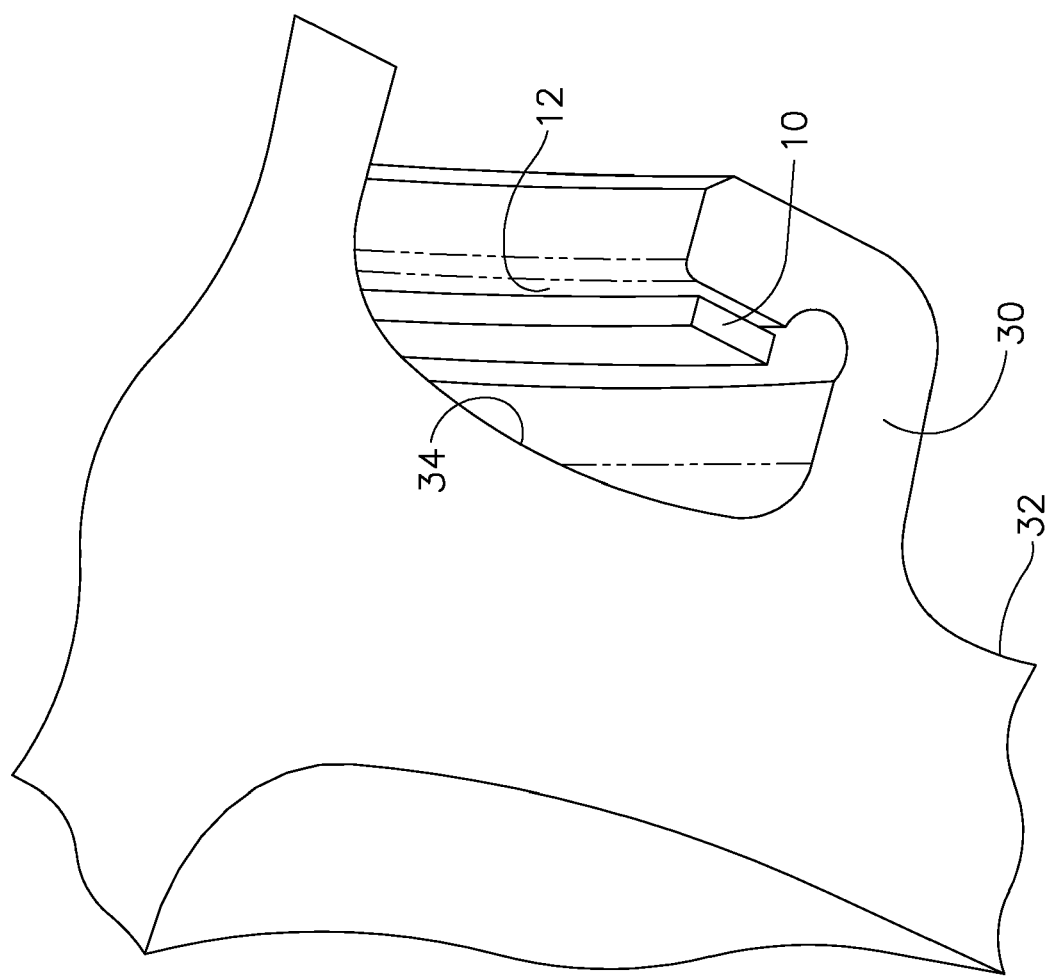
FIG. 2 is a perspective view illustration of a sub-size Almen test strip affixed to a disk facing shot peening surface on a hook of a gas turbine engine disk web.

Illustrated in FIGS. 1 and 2 are sub-size Almen test strips 10 affixed in situ to a shot peening surface 12 of a workpiece. In the exemplary methods of in situ measuring shot peening intensities disclosed herein, the Almen test strips 10 are affixed to the shot peening surfaces 12 by an adhesive such as rubber cement such that the Almen test strips 10 are flush against the shot peening surfaces 12. The in situ shot peening intensity measuring methods disclosed herein use full size standard Almen strips 48 and/or sub-size Almen test strips 10 having first and second sizes 42, 44 (see FIG. 3) that are smaller than the full size standard Almen strips 48. FIG. 1 illustrates a plurality of dovetail slots 14 between dovetail posts 16 carried on a rim 18 of a gas turbine rotor disk 20 which is representative of the workpiece. The Almen test strip 10, illustrated as a sub-size Almen test strip, is affixed with rubber cement to a difficult to access shot peening surface 12 in a pocket 22 of a dovetail slot 14. FIG. 2 illustrates a disk facing shot peening surface 12 on a hook 30 of a gas turbine engine disk web 32. The disk facing shot peening surface 12 is difficult to access with a shot peening stream and must rely on the shot peening stream ricocheting off a web surface 34 of the web 32 facing the shot peening surface 12. The Almen test strip 10 is affixed with rubber cement or some other method or adhesive means to the shot peening surface 12 on the hook 30 facing the web 32.

Figure 5:
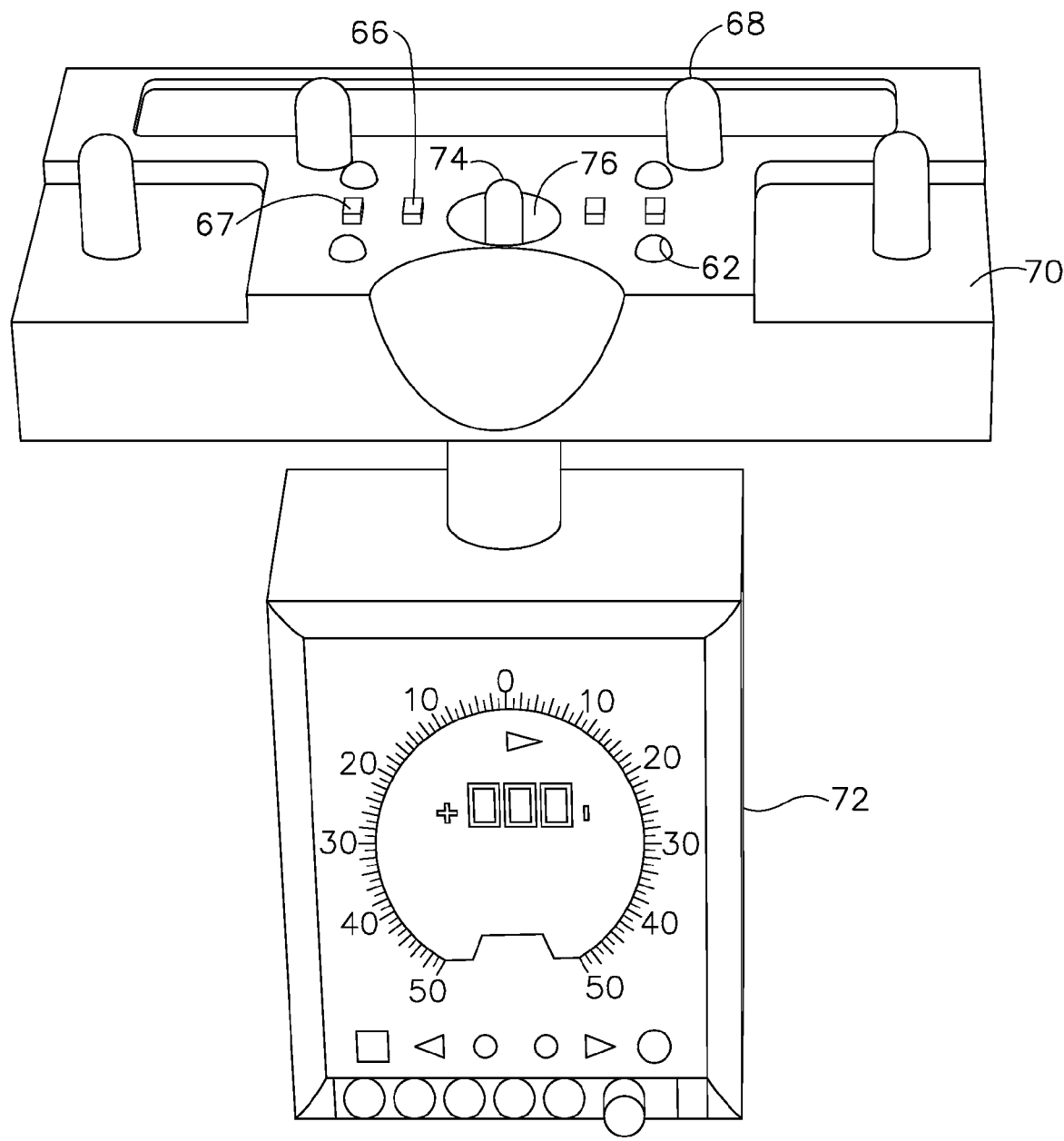
FIG. 5 is a perspective view illustration of a shot peening gage used to measure arc heights of the sub-size Almen strip and the standard size Almen strip.

After the Almen test strip 10 is affixed to the shot peening surface 12 with rubber cement or some other means or glue, the shot peening surface is shot peened at production shot peening conditions, the shot peened Almen test strip 10 is removed from the shot peening surface 12, and the arc height of the shot peened Almen test strip 10 is measured on an Almen gage 61 as illustrated in FIG. 5 to determine the shot peening intensity on the shot peening surface 12. The Almen gage 61 as illustrated in FIG. 5 includes a set of magnetic support balls 62 to hold a full size standard Almen strip 48 and second and third sets of magnets 66, 67 to hold first and second size 42, 44 sub-size Almen test strips 10 respectively. The second and third sets of magnets 66, 67 and the magnetic support balls 62 are mounted on a base 70 of the Almen gage 61. The second and third sets of magnets 66, 67 are set lower (e.g. 0.010 inches lower) than the magnetic support balls 62 so that arc height for differently sized Almen strips may be measured on the same Almen gage. The second and third sets of magnets 66, 67 are also set closer together than and are located inside of the magnetic support balls 62 so that the gage can accommodate three differently sized Almen strips. More than three differently sized Almen strips may be accommodated by adding more sets of magnets to hold more sub-size Almen strips.

A dial indicator 72 or digital indicator or other arc height measuring device has a spindle 74 which extends through a hole 76 in the base 70 to contact the strips and measure arc height in the shot peened strips. The second and third sets of magnets 66, 67 and the magnetic support balls 62 are centered around the hole 76 in the base 70 so that the arc height measuring device can measure the arc height of the three differently sized Almen strips. The Almen gage 61 includes end and rear locating first pins 68 for positioning the full size standard Almen strip 48 during measurement of the arc height of the full size standard Almen strip 48. Second and third sets of locating pins (not shown) for positioning the first and second size 42, 44 sub-size Almen test strips 10 may also be mounted on the base 70. The intensity, as a function of arc height, is either known or calibrated.

Figure 3:
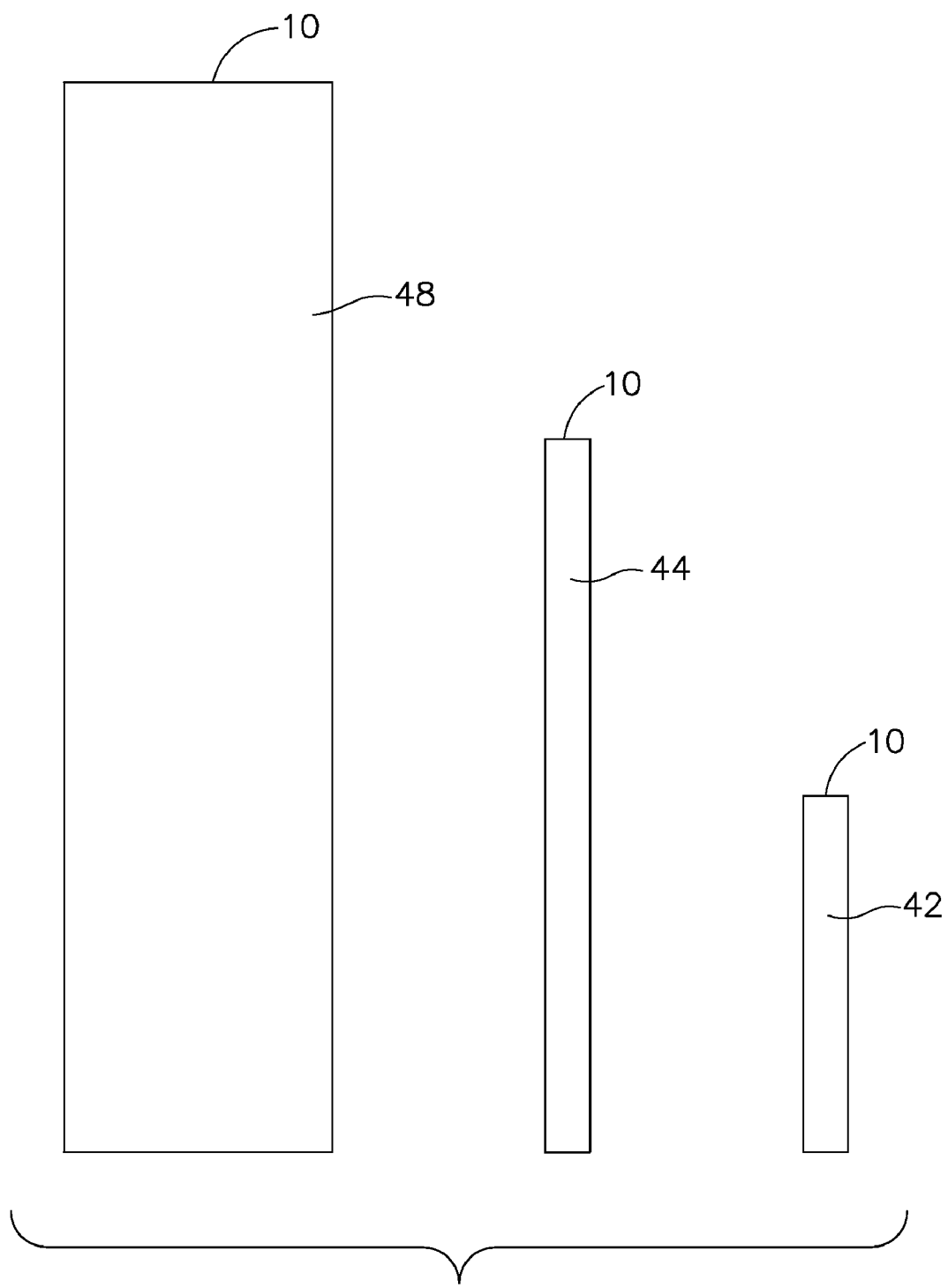
FIG. 3 is a cross sectional view illustration comparing a standard size Almen strip to two different sub-size Almen test strips cut from standard size Almen strips.

Referring to FIG. 3, Almen strips 48 typically come in standard sizes for which shot peening intensity as a function of arc height vs. time is known. Furthermore, it is well known how to determine shot peening intensity as a function of arc height for standard size Almen strips and Almen test strips peened only on a portion of the strip. It is also well known how to correlate intensity of Almen strips not bolted to holders to intensity of Almen strips bolted to the standard Almen block holder.

The Almen test strips 10 used in the exemplary method disclosed herein are sub-size test strips illustrated in the first and second sizes 42, 44 in FIG. 3 and which are cut from full size standard Almen strips 48 illustrated in FIG. 3. The first and second sizes 42, 44 illustrated herein are ⅛" in width and 1" and 2" in length, respectively. Standard size Almen test strips 48 are ¾" X 3" and include "A", "N" and "C" type Almen strips of different thicknesses. Cutting may be performed using an abrasive water-jet or by wire EDM or other low stress process.

Figure 6:
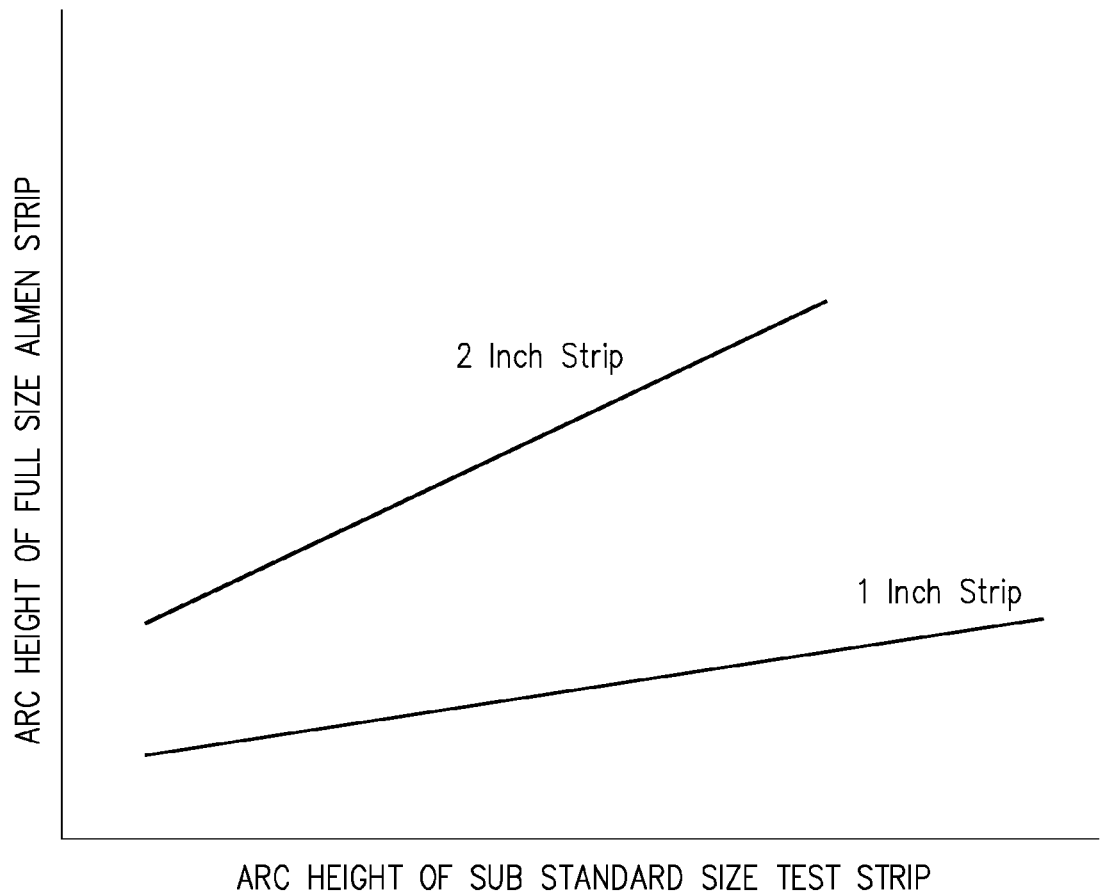
FIG. 6 graphic illustration of a correlation of arc height of the sub-size test strip to arc height of full size Almen strip.

The arc heights of the first and second size 42, 44 sub-size Almen test strips 10 may be correlated to arc heights of the standard size Almen strips 48 as illustrated in FIG. 6. Alternatively, the sub-size test strips may be independently calibrated to determine a correlation or function between shot peening intensity and arc height of the shot peened sub-size test strip. This correlation may be utilized in subsequent use of the sub-size strip.

Figure 4:
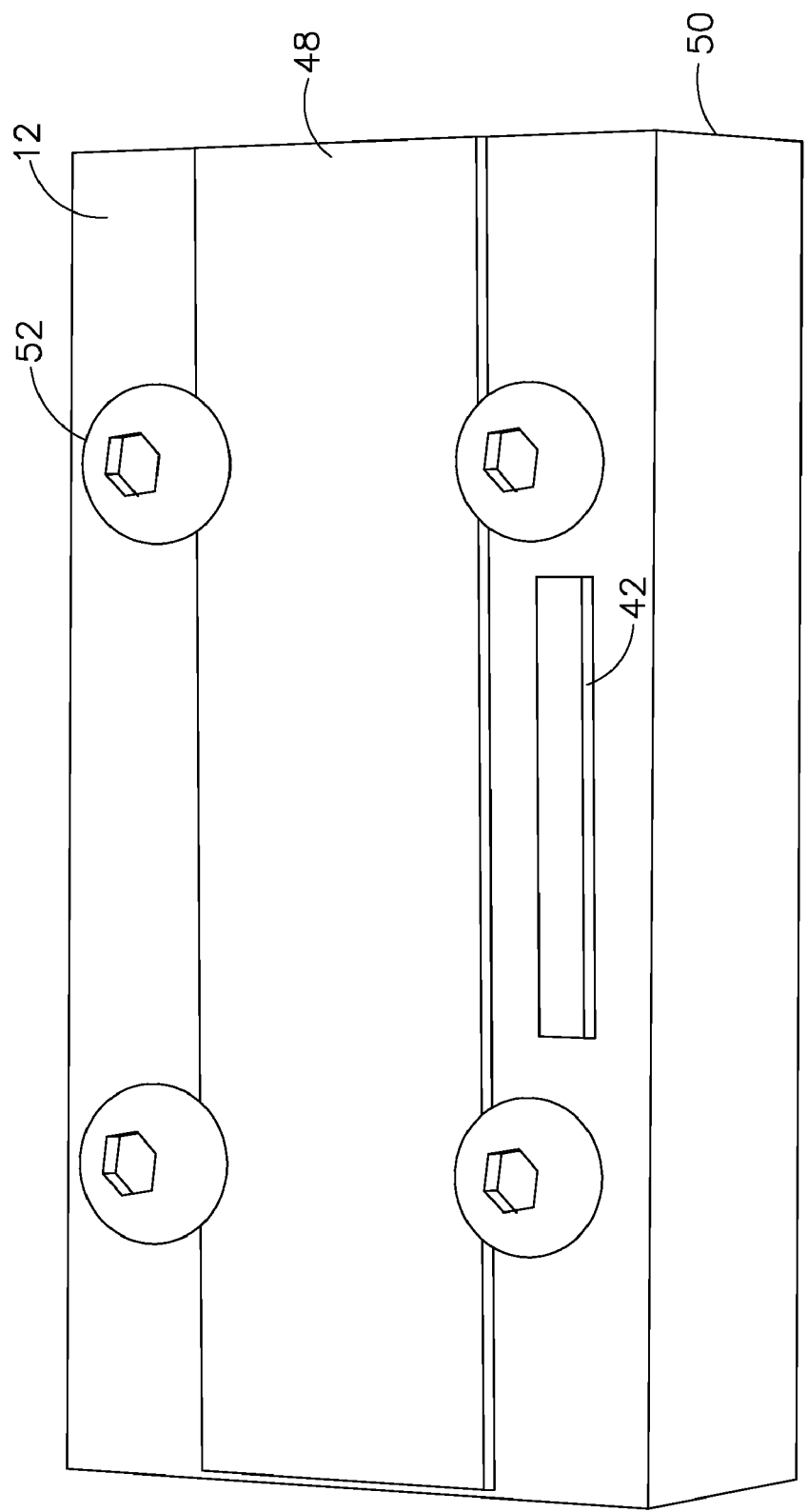
FIG. 4 is a perspective view illustration of a standard size Almen strip and a sub-size Almen test strip mounted on a shot peening block used to calibrate the sub-size Almen test strip against the standard size Almen strip at the same time the standard strip is being used to determine intensity on the part being peened.

Illustrated in FIG. 4 is a two strip shot peening block 50 with a sub-size Almen test strip 10 glued to a shot peening surface 12 of the block 50 and a full size standard Almen strip 48 conventionally mounted on the block 50 with screws 52. The two strip shot peening block 50 is useful for simultaneously shot peening the sub-size Almen test strip 10 and the full size standard Almen strip 48 for developing a correlation or function of shot peening intensity as a function of arc height of the sub-size Almen test strip 10 based on a known or previously determined correlation or function of shot peening intensity as a function of arc height of the full size standard Almen test strip 48. This correlation may be done at process set up.

Figure 7:
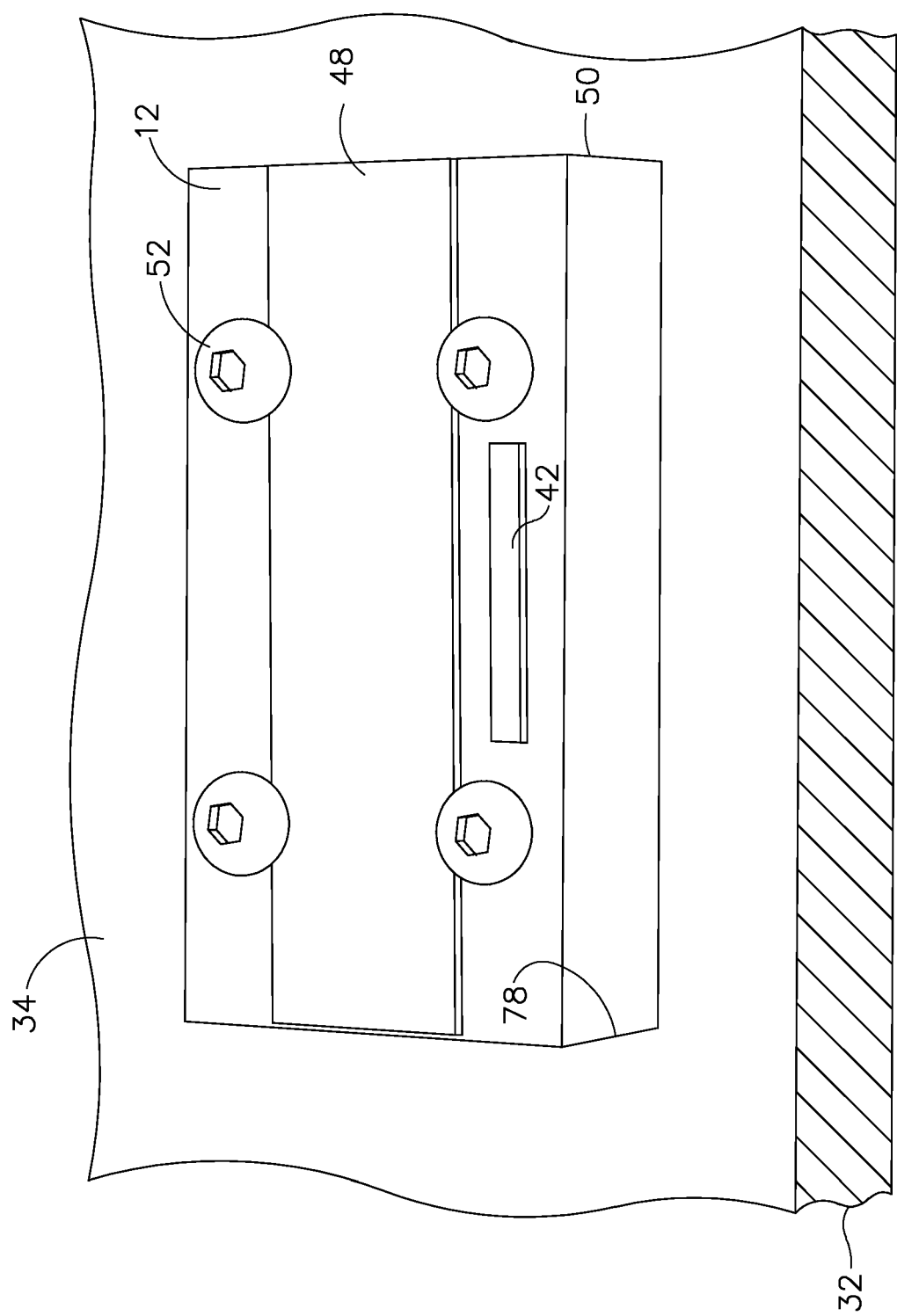
FIG. 7 is a cross-sectional view illustration of one of an Almen block affixed to a gas turbine engine disk web of a scrap disk.

The correlation mentioned above may be performed by mounting the two strip shot peening block 50 in a scrap part or workpiece as exemplified by the gas turbine rotor disk 20 in FIG. 7. The two strip shot peening block 50 is mounted in the gas turbine engine disk web 32 of the disk 20 within a receptacle 78. The two strip shot peening block 50 is mounted within the receptacle 78 that sized so that the shot peening surface 12 of the two strip shot peening block 50 is flush with the web surface 34 of the web 32. Then two strip shot peening block 50 is shot peened thereby simultaneously shot peening the sub-size Almen test strip 10 and the full size standard Almen strip 48. The simultaneous shot peening of the plurality of sub-size and standard strips around the part may be used to increase the statistical accuracy of the sub-size to standard strip arc height correlation. This correlation may also be performed by mounting one or more of the two strip shot peening blocks around a scrap or other part or workpiece and simultaneously shot peening the sub-size Almen test strips and the full size standard Almen strips mounted on the blocks.

While there have been described herein what are considered to be preferred embodiments of the present invention, other modifications of the invention shall be apparent to those skilled in the art from the teachings herein, and it is, therefore, desired to be secured in the appended claims all such modifications as fall within the true spirit and scope of the invention.

While the preferred embodiment of our invention has been described fully in order to explain its principles, it is understood that various modifications or alterations may be made to the preferred embodiment without departing from the scope of the invention as set forth in the appended claims.

What is claimed:

1. A method of determining shot peening intensity on a shot peening surface of a workpiece comprising the steps of:
   (a) cutting a sub-size Almen test strip cut from a full size standard Almen strip and using the sub-size Almen test strip as a Almen test strip;
   (b) affixing the Almen test strip to a shot peening surface;
   (c) removing the peened Almen test strip from the shot peening surface;
   (d) measuring an arc height of the shot peened Almen test strip; and
   (e) determining the shot peening intensity on the shot peening surface from the measured arc height and a correlation of arc heights of the sub-size Almen test strip to arc heights or shot peening intensities of the standard Almen strips.

2. A method as claimed in claim 1, further comprising using an adhesive for affixing the sub-size Almen test strip to the shot peening surface.

3. A method as claimed in claim 2, further comprising the adhesive being rubber cement.

4. A method as claimed in claim 1, further comprising using an A type Almen strip or an N type Almen strip or a C type Almen strip for the full size standard Almen strip.

5. A method as claimed in claim 4, further comprising using an adhesive for affixing the sub-size Almen test strip to the shot peening surface.

6. A method as claimed in claim 5, further comprising the adhesive being rubber cement.

7. A method of determining shot peening intensity on a shot peening surface of a workpiece comprising the steps of:
   (a) affixing an Almen test strip to a shot peening surface of a shot peening block;
   (b) removing the peened Almen test strip from the shot peening surface;
   (c) measuring an arc height of the shot peened Almen test strip;
   (d) determining the shot peening intensity on the shot peening surface from the measured arc height,
   cutting a sub-size Almen test strip cut from a full size standard Almen strip and using the sub-size Almen test strip as the Almen test strip,
   the determining the shot peening intensity includes correlating arc heights of the sub-size Almen test strip to arc heights or shot peening intensities of the standard Almen strips, and
   the determining the shot peening intensity includes mounting a full size standard Almen strip to the block and simultaneously shot peening the sub-size Almen test strip and the full size standard Almen strip mounted on the block.

8. A method as claimed in claim 7, further comprising:
   the correlating including measuring arc height of the shot peened sub-size Almen test strip and the full size standard Almen strip on an Almen gage,
   the Almen gage including a first support means for holding the full size standard Almen strip and one or more additional support means for holding the sub-size Almen test strip,
   the first and the one or more additional support means being mounted on a base of the Almen gage, and
   the first and one or more additional support means being sized and located for measuring the arc height of the full size standard Almen strip and the sub-size Almen test strip with a single dial or digital indicator or other arc height measuring device.

9. A method as claimed in claim 8 further comprising:
   the first support means including a set of magnetic support balls,
   the one or more additional support means including one or more additional sets of magnets,
   the one or more additional sets of magnets being set closer together than and being located inside of the magnetic support balls,
   the set of magnetic support balls and the one or more additional sets of magnets being centered around a hole in the base, and
   the dial or digital indicator or other arc height measuring device having a spindle extending through the hole in the base.

10. A method as claimed in claim 9, further comprising using an adhesive for affixing the Almen test strip to the shot peening surface.

11. A method as claimed in claim 10, further comprising the adhesive being rubber cement.

12. A method as claimed in claim 9, further comprising using an A type Almen strip or an N type Almen strip or a C type Almen strip for the full size standard Almen strip.

13. A method as claimed in claim 12, further comprising using an adhesive for affixing the Almen test strip to the shot peening surface.

14. A method as claimed in claim 13, further comprising the adhesive being rubber cement.

15. A method of determining shot peening intensity on a shot peening surface of a workpiece comprising the steps of:
   (a) affixing a sub-size Almen test strip to a shot peening surfaces of a shot peening block mounted on a workpiece,
   (b) mounting a full size standard Almen strip to the block,
   (c) simultaneously shot peening the sub-size Almen test strip and the full size standard Almen strip mounted on the block,
   (d) measuring an arc height of the shot peened sub-sized Almen test strip and measuring an arc height of the shot peened full size standard Almen strip,
   (e) correlating the arc height of the shot peened sub-size Almen test strip to the arc height of the standard Almen strip, and (f) determining the shot peening intensity on the shot peening surface from the measured arc height from the shot peened sub-sized Almen test strip and correlation of the arc height of the shot peened sub-size Almen test strip to the arc height of the standard Almen strip.

16. A method as claimed in claim 15, further comprising:
the correlating including measuring the arc height of the shot peened sub-size Almen test strips and the arc height of the full size standard Almen strip on an Almen gage,
the Almen gage including a first support means for holding the full size standard Almen strips and one or more additional support means for holding the sub-size Almen test strip,
the first and the one or more additional support means being mounted on a base of the Almen gage, and
the first and the one or more additional support means being sized and located for measuring the arc height of the full size standard Almen strip and the arc height of the sub-size Almen test strip with a single arc height measuring device.

17. A method as claimed in claim 16 further comprising:
the first support means including a set of magnetic support balls,
the one or more additional support means including one or more additional sets of magnets,
the one or more additional sets of magnets being set closer together than and being located inside of the magnetic support balls, and
the set of magnetic support balls and the one or more additional sets of magnets being centered around a hole in the base.

18. A method as claimed in claim 17 further comprising the dial or digital indicator or the other arc height measuring device having a spindle extending through the hole in the base.

19. A method as claimed in claim 17, further comprising using an adhesive for affixing the Almen test strips to the shot peening surfaces.

20. A method as claimed in claim 19, further comprising the adhesive being rubber cement.

21. An Almen gage comprising:
a first support means for holding a full size standard Almen strip,
one or more additional support means for holding a sub-size Almen test strip,
the first and the one or more additional support means being mounted on a base of the Almen gage, and
the first and the one or more additional support means being sized and located for measuring an arc height the full size standard Almen strip and the sub-size Almen test strip with a single dial or digital indicator or other arc height measuring device fixed relative to the base.

22. An Almen gage as claimed in claim 21, further comprising:
the first support means including a set of magnetic support balls,
the one or more additional support means including one or more additional sets of magnets,
the one or more additional sets of magnets being set closer together than and being located inside of the magnetic support balls, and
the set of magnetic support balls and the one or more additional sets of magnets being centered around a hole in the base.

23. An Almen gage as claimed in claim 22, further comprising the dial or digital indicator or the other arc height measuring device having a spindle extending through the hole in the base.

* * * * *